(12) United States Patent
Fraenkel et al.

(10) Patent No.: US 6,526,803 B1
(45) Date of Patent: Mar. 4, 2003

(54) APPARATUS AND METHOD FOR GENERATING MOISTURE STANDARDS IN GASES

(75) Inventors: Dan Fraenkel, Boulder, CO (US); Gerald Cooper, Boulder, CO (US)

(73) Assignee: Matheson Tri-Gas, Inc., Longmont, CO (US)

( * ) Notice: Subject to any disclaimer, the term of this patent is extended or adjusted under 35 U.S.C. 154(b) by 0 days.

(21) Appl. No.: 09/388,084

(22) Filed: Aug. 31, 1999

(51) Int. Cl.[7] ............................................... G01N 31/06

(52) U.S. Cl. ........................................................ 73/1.04

(58) Field of Search ................................. 73/1.01–1.07; 261/34.1, 100, 101, 103, 104, 106, 94, 95, 97, DIG. 65

(56) References Cited

U.S. PATENT DOCUMENTS

| | | | |
|---|---|---|---|
| 911,875 A | 2/1909 | Hastings | |
| 943,638 A | 12/1909 | Webb et al. | |
| 1,303,187 A | 5/1919 | Ferrell | |

(List continued on next page.)

FOREIGN PATENT DOCUMENTS

SU           928291    *  5/1982  ................. 73/1.06

OTHER PUBLICATIONS

Don E. Pivonka, *The Infrared Spectroscopic Determination of Moisture in HCl for the Characterization of HCl Gas Drying Resin Performance*, Applied Spectroscopy 45(4):597–602 (Nov. 1991).

Peter A. Huang, *Accuracy of PPM Humidity Standard Based on Permeation Method*, Proceedings of the Sixth International Meeting on Chemical Sensors, National Institute of Standards and Technology, Gaithersburg, Md. (Jul. 22–25, 1996).

(List continued on next page.)

*Primary Examiner*—Robert Raevis
(74) *Attorney, Agent, or Firm*—Steven C. Petersen; Sarah S. O'Rourke; Hogan & Hartson LLP (57) ABSTRACT

An apparatus and method for generating moisture standards in gases are disclosed. In particular, the invention relates to an apparatus for introducing a preselected amount of water vapor or other vaporized liquid into a flowing gas stream at a constant rate, which comprises a suitable syringe having a needle attached thereto; an evaporator attached to said needle, wherein the evaporator is located in the flowing gas stream; and a means for applying pressure to the syringe, such that water or other liquid may be delivered at a constant rate from the syringe through the needle into the evaporator. The invention also relates to a method for introducing a preselected amount of water vapor or other vaporized liquid into a flowing gas stream at a constant rate, which comprises providing a syringe having a needle attached thereto, wherein the syringe contains the water or other liquid to be vaporized; applying pressure to the syringe, such that water or other liquid is transferred at a constant rate from the syringe through the needle into an evaporator, said evaporator being attached to one end of the needle, and situated in the flowing gas stream; and allowing the water or other liquid to evaporate from the evaporator into the flowing gas stream. The apparatus and method of the invention are useful for the generation of low levels of moisture, and are especially useful where quick and reliable changes of moisture level in the gas is desired. Thus, the apparatus and method are useful in the generation of primary moisture standards for use in the calibration of moisture analyzing instruments, such as FTIR spectrometers.

33 Claims, 8 Drawing Sheets

U.S. PATENT DOCUMENTS

| | | | | | |
|---|---|---|---|---|---|
| 2,354,064 | A | | 7/1944 | Rose | |
| 3,592,182 | A | | 7/1971 | Richardson | |
| 3,948,604 | A | * | 4/1976 | Hoppesch | 73/1.05 |
| 4,036,915 | A | * | 7/1977 | Lucero et al. | 73/1.04 |
| 4,063,446 | A | * | 12/1977 | Fuhrmann | 73/1.06 |
| 4,164,861 | A | * | 8/1979 | Schlereth et al. | 73/1.04 |
| 4,170,455 | A | | 10/1979 | Henrie | |
| 4,975,249 | A | | 12/1990 | Elliot | |
| 5,325,705 | A | | 7/1994 | Tom | |
| 5,407,269 | A | * | 4/1995 | Sherry et al. | 73/1.05 |
| 5,457,983 | A | * | 10/1995 | Sauvageau et al. | 73/1.06 |

OTHER PUBLICATIONS

P. Jaakkola et al. *Instrumental Resolution Considerations for Fourier Transform Infrared Gas–Phase Spectroscopy*, Applied Spectroscopy 51(8):1159–1169 (Nov. 1997).

Tekran, Inc., *Summary of Mercury Analysis Products* (visited May 19, 1999) <http.//tekran.com/products.html>.

Tekran, Inc., *Model 2505—Mercury Vapor Calibration Unit* (visited May 19, 1999) <http://tekran.com/2505/2505fea.html>.

Tekran, Inc., *Model 2505—Principles of Operation* (visited May 19, 1999) <http://tekran.com/2505/2505poi.html>.

Tekran, Inc., *Tips on Making Saturated Mercury Vapor Injections* (visited May 19, 1999) <http://tekran.com/2505/2505inj.html>.

* cited by examiner

APPARATUS AND METHOD FOR GENERATING MOISTURE STANDARDS IN GASES

1. FIELD OF THE INVENTION

The present invention relates to an apparatus and method for generating moisture standards of known water concentrations in gases. The method and apparatus of the invention utilize volumetric measurement of water delivered to the gas to calculate the resulting water concentration. In particular, the method and apparatus of the invention provide for delivery of a preselected amount of water vapor to a flowing gas stream, thus enabling quick and reliable calculation of the resulting concentration of water in the gas.

2. BACKGROUND OF THE INVENTION

Measurement of low levels of moisture content in dry gases is critical for applications in which high or ultrahigh purity gases are used. For example, the measurement of ppb levels of moisture in ultrahigh purity gases used in the microelectronics or semiconductor industries is crucial. Moisture is one of the most ubiquitous and serious contaminants in the fabrication of microelectronic devices, such as wafers. Its presence in the gas phase can lead directly to impaired wafer yield. Moisture in certain gases used in fabrication of microelectronic devices can also accelerate the corrosion of tubing, regulators and valves used in handling these gases, and the corrosion products can negatively impact wafer yields and quality. Therefore, stringent measurement and control of moisture as a contaminant is required.

Instruments which can be used to measure moisture at such low levels include electrolytic cells, dielectrics of polymer/ceramic, vibration crystals, Fourier transform infrared (FTIR) spectrometers, atmospheric pressure ionization mass spectrometers, and chilled-mirror frost-point hygrometers. These instruments generally require calibration using gases with known moisture content. For example, FTIR analysis of moisture in a gas requires the generation of a calibration curve of absorbance due to water at a selected wavelength, versus known concentration of water in that gas. In order to generate such a calibration curve, gas standards with known concentrations of water are necessary. In addition, it is often necessary to check the response of a moisture meter used to monitor the moisture level in a gas, requiring a gas having a known water concentration, or "humidity challenge." Moreover, measurement of the corrosion of steel as a function of the moisture contamination in hydrogen chloride gas requires the generation of gas standards having known concentrations of water vapor.

Such calibration gases are typically produced using moisture standard generators. There are currently two primary methods for generating known concentrations of water vapor in a flowing gas: permeation tubes and diffusion vials.

Permeation tubes are containers having a permeable polymeric membrane and that are filled with water. The tubes are placed in a flowing dry gas stream, and water vapor permeates through the membrane and into the dry gas. Permeation tubes operate on the principle that the amount of water permeating through the membrane is constant at a constant temperature. The resultant water vapor concentration in the flowing dry gas is determined by multiplying the molar gas constant for water vapor by the permeation rate, and dividing by the gas flow rate. To produce standards having different moisture concentrations, either tubes having membranes with different emissivities must be employed, or the flow rate of the gas must be varied.

Permeation tubes are the most widely employed moisture standard generators, perhaps because of their convenience. However, problems with the reliability of these devices often occur. One problem is that the moisture emitted from the permeation tube is highly dependent on the control of temperature and pressure. Thus, slight variations in the temperature or pressure of the flowing dry gas will cause the resultant moisture content of the gas to vary significantly.

A potentially more serious problem with permeation tubes is the deviation of the tubes from their claimed accuracy. In experiments or calibrations using moisture standards, complex ancillary equipment is often used, making it difficult to ascribe irregularities that may arise in the measurements to a particular causative agent. Therefore, the moisture standard generator itself should be as reliable as possible. Although initial calibration of the manufacturer's equipment is performed with National Institute of Standards and Technology (NIST) traceable standards, a user employing a particular permeation tube must depend upon the continued validity of the manufacturer's calibration. It has been shown that permeation tubes may be in error of their reported values by as much as about 30% around 1 ppm when compared to NIST humidity standards validated by an optical frost-point hygrometer. See Huang, Peter A., "Accuracy of PPM Humidity Standard Based on Permeation Method," Proceedings of the Sixth International Meeting on Chemical Sensors, National Institute of Standards and Technology, Gaithersburg, Md. (Jul. 22–25, 1996).

If the reliability of permeation tubes is suspect, calibration may be verified using commercially available moisture meters. However, these meters are expensive and are themselves often inaccurate, unreliable and responsive over only narrow concentration ranges. Another recourse is to send the tube back to the manufacturer for re-calibration, but this is very time consuming and inconvenient. A third alternative is that the calibration could be performed in-house. However, this would be impractical and extremely inconvenient, as the calibration would require NIST traceable standards, proper equipment and experienced personnel.

Diffusion vials offer a significant increase in certainty at the expense of convenience and flexibility. A diffusion vial system consists of a bottle of water having a small hole at the top and contained in a temperature-controlled housing. The water is introduced into an inert dry gas by flowing the gas over the vial opening. The system operates on the principle that the vapor pressure of water, and therefore the rate of release of water vapor from the vial, is constant at a constant water temperature. Thus, once the system reaches a steady temperature and constant flow rate, the rate of water introduced into the dry gas is theoretically constant.

The main advantage of this system is that the total amount of water introduced into the dry gas can be accounted for gravimetrically, i.e. the exact quantity of water introduced into the flowing gas stream can be determined by weighing the vial before and after use. However, a significant problem with the diffusion vial is that it is impractical to obtain values of the water concentration before the end of the experiment for two reasons. First, obtaining water consumption rates essentially requires stopping the experiment because one must stop the gas flow, disconnect the gas lines, remove the vial and weigh it. Hence, any measurement of concentration will necessarily be performed at the end of the experiment, making intermediate water consumption rates impossible to obtain. Second, the diffusion vial is sensitive to temperature, pressure and water level, and disturbing these conditions by stopping the gas flow and disconnecting the gas lines will affect the rate of diffusion. Therefore, the diffusion vial method of generating moisture standards is more suited to providing an accurate average, rather than instantaneous, water concentration.

Another problem with the diffusion vial system is that this method is useful only over a relatively high concentration range, i.e. thousands of ppm. To achieve lower concentrations of water, one could attempt to pass higher flow rates of gas over the vial, but this leads to temperature control problems. Another solution is to dilute the highly concentrated vapor and reject the excess flow. However, this requires dilution apparatus and flow meters, each having uncertainties of their own, and these errors would combine additively thereby diminishing the accuracy of the moisture concentration.

U.S. Pat. No. 3,592,182 to Richardson discloses an apparatus for humidifying air flowing through a furnace duct for room use. The humidifier is designed for installation within the confines of a horizontal furnace duct. The humidifier comprises a hollow shell which is constructed to provide a container for a predetermined amount of water. The water level in this container is maintained by a float valve. A sponge is positioned within the hollow shell. As the air stream from the furnace blower flows across the moistened sponge, it is humidified for room use.

The humidifier disclosed by Richardson is unsuitable for use as a moisture standard generator for several reasons. Most significantly, this humidifier has no means for quickly and unobtrusively varying the amount of water introduced into the air stream. The water in the hollow shell is maintained at a constant level by a float valve, and this level cannot be changed without stopping the air flow, dismantling the air duct, and changing the position of the float valve. The rate of water delivery to the sponge is always equal to the maximum rate of evaporation from the sponge, which is determined by the temperature and flow rate of the air stream. Moreover, very low levels of moisture, i.e. the ppb levels of interest in microelectronics or semiconductor industries, cannot be generated with this humidifier. In addition, the humidifier of Richardson can be used only in a horizontal portion of a duct.

Accordingly, there is a need in the art for a moisture standard generator capable of introducing a constant, preselected amount of moisture into a dry matrix gas, in which the amount of moisture can be varied easily, reliably and quickly, without the use of complicated dilution equipment. There is also a need in the art for a moisture standard generator which is not sensitive to temperature, and which is suitable for operation at ambient temperature and pressure.

3. SUMMARY OF THE INVENTION

The present invention obviates many of the problems associated with conventional moisture standard generators by providing an apparatus and method for introducing a known amount of water vapor into a gas, which uses volumetric measurements to determine the amount of water introduced, rather than the gravimetric measurements relied on by diffusion vials, or the manufacturer-dependent emissivity rates of permeation tubes. Thus, the present invention relates, in part, to an apparatus for introducing a preselected amount of water vapor into a flowing gas stream at a constant rate, which comprises: (a) a syringe comprising a housing and a plunger, and having a needle attached thereto, (b) an evaporator, said evaporator being attached to the end of the needle, wherein the evaporator may be situated in a flowing gas stream, and (c) a means for moving the plunger of the syringe at a constant speed. The water to be used in generation of the moisture standard is contained within the syringe housing. Pressure is applied to the syringe to move the syringe plunger at a constant speed such that water is transferred from the syringe into the evaporator at a constant rate. The water introduced into the evaporator simultaneously evaporates at a constant rate into the flowing gas stream, thereby generating a moisture standard with a known concentration of water vapor.

Accordingly, in one embodiment, the present invention relates to an apparatus for introducing a preselected amount of water vapor into a flowing gas stream at a constant rate, which comprises: (a) a syringe having a needle attached thereto; (b) an evaporator, said evaporator being attached to one end of the needle, wherein the evaporator may be located in the flowing gas stream; and (c) a means for applying pressure to the syringe, such that water may be delivered at a constant rate from the syringe through the needle into the evaporator. Pressure is applied to the syringe such that the plunger of the syringe moves at a constant rate, thereby dispensing liquid from the syringe to the evaporator at a constant rate.

The present invention also encompasses a method for introducing a preselected amount of water vapor into a flowing gas stream at a constant rate, which comprises: (a) providing a syringe having a needle attached thereto, wherein the syringe contains liquid water; (b) applying pressure to the syringe, such that an amount of water is transferred from the syringe through the needle into an evaporator at a constant rate, said evaporator being attached to one end of the needle, and situated in the flowing gas stream; and (c) allowing the water to evaporate from the evaporator into the flowing gas stream. In a preferred embodiment, the evaporator is a piece of material, such as felt, which is attached to one end of the needle. The other end of the needle is attached to the syringe.

In addition to water, many other liquids may be used in the apparatus and method of the present invention. Thus, the present invention also relates to an apparatus for introducing a preselected amount of vaporized liquid into a flowing gas stream at a constant rate, which comprises: (a) a syringe having a needle attached thereto; (b) an evaporator, said evaporator being attached to one end of said needle, wherein the evaporator may be located in the flowing gas stream; and (c) a means for applying pressure to the syringe, such that the liquid to be vaporized may be delivered at a constant rate from the syringe through the needle into the evaporator.

The present invention also relates to a method for introducing a preselected amount of vaporized liquid into a flowing gas stream at a constant rate, which comprises: (a) providing a syringe having a needle attached thereto, wherein the syringe contains the liquid to be vaporized; (b) applying pressure to the syringe, such that an amount of the liquid to be vaporized is transferred from the syringe through the needle at a constant rate into an evaporator, said evaporator being attached to one end of the needle, and situated in the flowing gas stream; and (c) allowing the liquid to evaporate from the evaporator into the flowing gas stream; wherein the amount of vaporized liquid is selected to result in a preselected concentration of the vaporized liquid in the flowing gas stream.

The apparatus and method of the present invention enable the user to determine the resulting concentration of moisture or other vaporized liquid in the gas quickly and conveniently, without stopping the flow of gas and opening the gas delivery system. When necessary the syringe can be easily disconnected from the needle, removed from the apparatus, refilled with water or other liquid and reconnected (or replaced with a full syringe), with only minimal disturbance to the system. Similarly, the syringe can be disconnected and replaced with a syringe having a larger or smaller volume, thereby permitting the concentration of moisture or other vaporized liquid to be varied easily, reliably and quickly without interrupting the gas flow. By selecting the appropriate size syringe, rate of syringe compression, and the flow rate of the gas stream, a wide range of moisture concentrations or concentrations of other vaporized liquids can be achieved with the apparatus and method of the present invention, without the use of complicated dilution apparatus, and with minimal disturbance to gas handling systems.

4. BRIEF DESCRIPTION OF THE DRAWINGS

FIG. 1A depicts an embodiment of the apparatus of the present invention, which was used in Example 6.1. The apparatus comprises a syringe 7 which comprises a body 8, a plunger 9 and a needle 3. The needle has an evaporator attached to its open end such that the evaporator may be situated inside the tube 10, also referred to herein as a receptacle, which comprises an inlet 1 and outlet 2, and which contains the flowing gas stream 11. The tube 10 may comprise an optional viewing port 4, for visual inspection of the interior of the receptacle to verify total evaporation of water, and optional stainless steel screens 5 and 6 which serve as gas flow straighteners.

FIG. 1B is an enlargement of the area in FIG. 1A enclosed by the dashed circle.

FIG. 2 also depicts the optional glass viewing port 4.

FIG. 3 is a schematic view of an experimental system which can be used to generate moisture standards in nitrogen gas using the apparatus and methods of the present invention. The system comprises a source of dry nitrogen 1, the pressure of which is regulated to about 5 psi outlet pressure with pressure regulator 2; rotameters 3 and 4; the volumetric moisture generator of the present invention 5 (i.e., the apparatus of the present invention for introducing a preselected amount of water vapor into a flowing gas stream); an FTIR spectrometer 6 equipped with a ten-meter gas cell 7; valves 8 and 9 that allow the nitrogen to pass through tubing 10, either directly to the FTIR cell 7 through bypass line 15, when valve 8 is open and valve 9 is closed, in order to obtain blank or zero reference measurements, or when changing or replacing the syringe of the volumetric moisture generator 5, or through the volumetric moisture generator 5 to be humidified by having valve 8 closed and valve 9 open; MKS Baratron pressure transducers 11 and 12; and check valve 13. The gas flows out of the FTIR cell 7 through vent 14.

FIG. 4 demonstrates the rapid response of the apparatus of the invention to changes in moisture concentration generated according to the methods of the invention.

5. DETAILED DESCRIPTION OF THE INVENTION

The present invention is directed to an apparatus for generating a moisture standard in flowing gas stream, which comprises a syringe, an evaporator attached to the needle of the syringe, and a means for applying pressure to the syringe such that liquid water may be dispensed from the syringe at a constant rate. The present invention also relates to a method for generating moisture standard in a flowing gas stream which comprises: (a) providing a syringe, said syringe comprising a body, a plunger, and a needle having an evaporator attached thereto, wherein the syringe contains liquid water; (b) moving the plunger of the syringe at a constant speed such that water is transferred at a constant rate from the syringe into the evaporator, and (c) allowing water to evaporate from the evaporator into the flowing gas stream. The apparatus and method of the invention are suitable for the generation of standards of any vaporizable liquid in a flowing gas.

In accordance with the method of the present invention, pressure is applied to the syringe so that water is delivered to the evaporator at a constant rate. So long as the water evaporates completely from the evaporator, the rate of water introduction into the flowing gas stream is also constant. Therefore, the speed with which the syringe is compressed and the size of the syringe control the rate of water vaporization. The resulting concentration of water vapor in the flowing gas stream may be easily calculated from the change in the volume of water in the syringe (i.e., the amount of liquid water dispensed from the syringe), the interval of time during which the water was dispensed, and the flow rate of the flowing gas stream. Thus, the water concentration of the moisture standard generated in the flowing gas stream according to the methods of the present invention can be measured immediately and conveniently without stopping the experiment, by measuring the volume indicated on the syringe scale. The accuracy of the determination of moisture concentration depends only on the accuracy of the volumetric calibration of the syringe, the consistency of the speed at which the plunger of the syringe is moved, and the accuracy of the gas flow meter. Unlike conventional methods of moisture standard generation, the apparatus and method of the present invention are insensitive to small variations in temperature and pressure.

The ability to quickly and easily determine the concentration of the moisture standard generated in accordance with the present invention, makes the method and apparatus of the invention particularly useful in the generation of primary moisture standards, i.e., moisture standards that can be used to generate a calibration curve for a particular instrument, such as an FTIR spectrometer, or that can be used to calibrate other moisture detection equipment. Moreover, the concentration of vapor generated according to the methods of the present invention can be varied easily and quickly by merely varying the speed at which the plunger of the syringe is compressed. Other advantages of the present invention include insensitivity of the method to temperature, provided ambient conditions can supply enough heat to evaporate all the injected water; and ability to operate at ambient pressures.

The methods and apparatus of the present invention provide the user with the flexibility to generate moisture standards in gases having a wide range of concentrations without the use of complicated dilution equipment. The method and apparatus of the invention are suitable for generation of moisture standards ranging, for example, from about 1 ppb to about 10,000 ppm in water concentration; preferably, from about 10 ppb to about 1000 ppm. The method and the apparatus of the invention are particularly suited for generating moisture standards in range of about 10 ppm to about 800 ppm.

In addition to water, there are many other liquids that may be used in the method and apparatus of the present invention. In particular, the method and apparatus of the present invention are suitable for generating standards of organic liquids, including solvents such as acetone, methylene chloride, acetonitrile, benzene, toluene, to name a few, in various matrix gases. Further, the methods and apparatus of the present invention are suitable for generating standards of organometallic liquids in gases. The methods and apparatus of the present invention are appropriate for generating standards of any liquid that may be evaporated into a flowing matrix gas stream.

Generally, the wavelength of the water absorbance peak used to generate an FTIR calibration curve is selected based on the matrix gas being used. For example, certain matrix gases such as hydrogen chloride (HCl) have absorbance peaks that appear close to, or at the same wavenumber as water peaks in the FTIR spectrum. In such cases, the water peak used for generating the calibration curve must be chosen so that it does not interfere with the matrix gas peaks.

In accordance with the method of the present invention, the evaporator, which is attached to the needle of the syringe, is located in the flowing gas stream. Typically, the flowing gas stream is contained within a system of tubing. Any tubing which is compatible with the flowing gas stream may be used. For example, copper tubing with an 0.5 inch (about 1.3 cm) diameter may be used. However, other sizes of tubing, such as 0.25 inch or 1.00 inch (about 0.6 cm or 2.5 cm) are appropriate. Tubing made of materials such as stainless steel, Teflon, polyethylene, nickel, or other suitable material is also appropriate for use in the present invention.

Figures 1A, 1B:
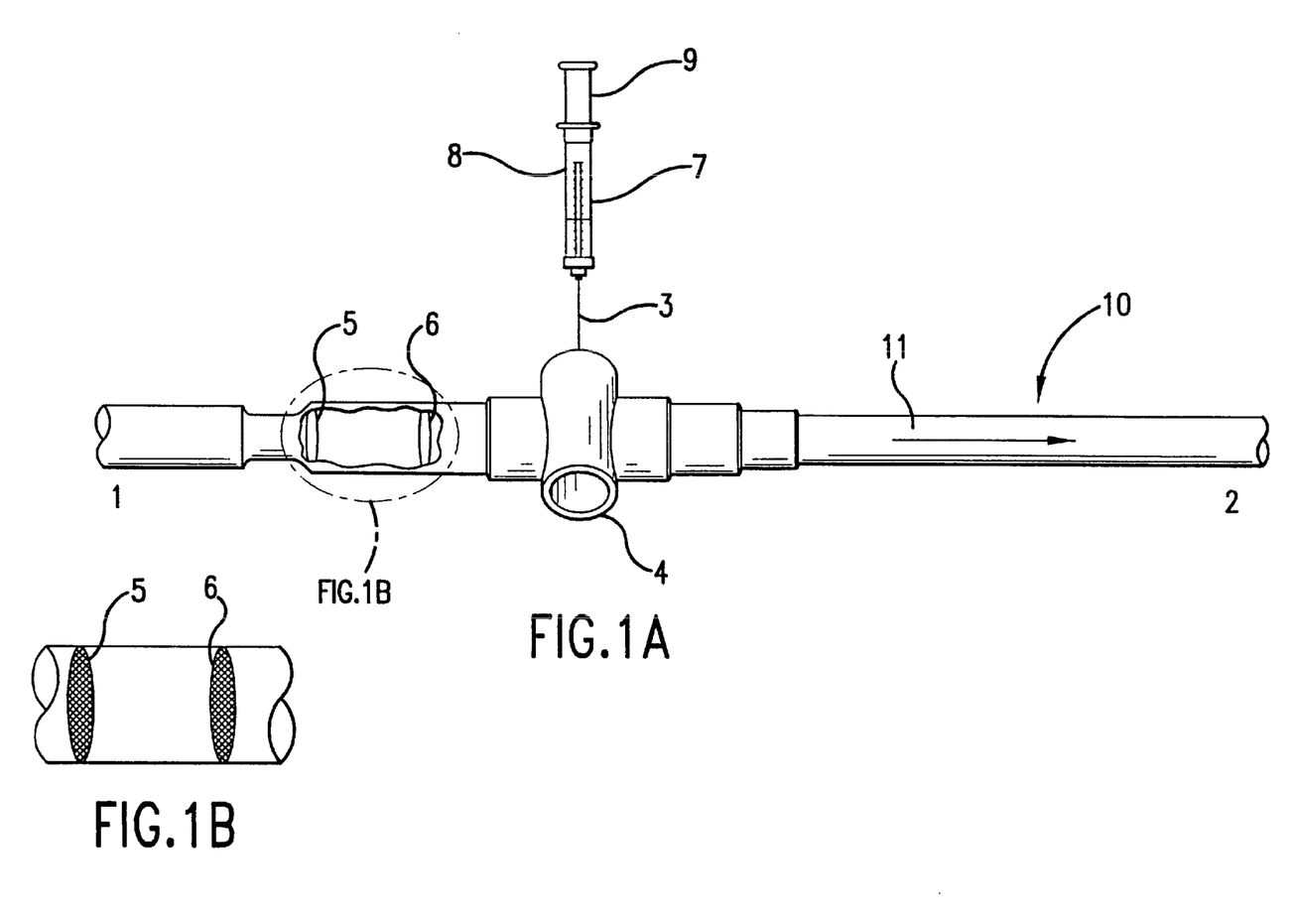

In one embodiment, the evaporator is contained within a receptacle which may be inserted into the gas line containing the flowing gas stream. An example of such a receptacle is shown in FIG. 1A and is described in detail in Example 6.1 below. In one embodiment, the receptacle itself is a piece of tubing, about 17 inches (about 44 cm) long, preferably copper tubing having a diameter of 0.5 inch (about 1.3 cm). The receptacle is equipped with firings at both ends of the tubing, so that the receptacle can be installed directly into the gas line which contains the flowing gas stream in which the moisture standard is to be generated. The needle of the syringe is affixed to the tubing at an angle, preferably at 90° angle, through a hole in the side of the rubing, and soldered or glued in place, such that the open end of the needle (i.e., the tip of the needle) is located inside the tubing, while the other end of the needle, i.e., the end of the needle that is attached to the syringe, is located outside the tubing. In another embodiment, the receptacle may comprise a "T" fitting in which the needle is affixed to the receptacle through the perpendicular arm of the T-fitting. The needle may be soldered or glued in place, or it may be attached using the appropriate fitting. The T-fitting receptacle may be installed directly into the gas line containing the flowing as in which the moisture standard is to be generated.

Any syringe suitable for handling the vaporizable liquid may be used in the apparatus and method of the invention. The size of the syringe should be selected based on the flow rate of the gas and the desired vapor concentration to be generated in the gas. The syringe of the present invention is preferably a "gas-tight" syringe of the type typically used in gas chromatography applications. For example, gas-tight 2.5-ml and 250 $\mu$l syringes manufactured by Hamilton are suitable for use in the apparatus and method of the present invention. "Gas tight" syringes are preferred because of their ability to contain liquid without evaporation or leakage. The term "syringe" as used herein refers to any standard syringe having a barrel, also referred to herein as the body or housing of the syringe, a plunger which is matched to the barrel, a tip, and a hollow needle of the type typically used for injections. The needle is attached to the tip of the syringe. Preferably, the body of the syringe is glass; however, syringes made of other materials such as plastic or metal may be used. In a preferred embodiment, the barrel of the syringe is marked with volumetric calibrations, such that the volume of liquid dispensed may be easily determined through visual inspection. The plunger of the syringe is preferably equipped with a gas tight seal, preferably composed of rubber or Teflon.

It is preferred that the needle of the syringe be easily detached from the syringe; however, syringes with fixed needles (i.e., glued) may be used. Preferably, the needle is attached to the syringe using a Luer-Lok fitting, or other such attachment means well known to those skilled in the art.

The needle may be made of any metal; however, the needle is preferably made of stainless steel. Alternatively, needles made of other materials such as plastic or Teflon may be used. As mentioned above, it is preferred that the needle may be easily detached and reattached to the syringe, such that syringes of different sizes or containing various amounts of liquid may be attached and detached from the same needle. The diameter (i.e., the gauge) of the needle used in a particular application will depend on the size of syringe used, and on the amount of liquid to be delivered. For example, an RN needle of 22S gauge is appropriate for use with a 250 $\mu$l syringe; and a 22 gauge needle is appropriate for use with a 2.5 ml syringe. The needle may be of any length, as long as the needle is long enough to extend into the tubing containing the flowing gas stream while being attached to the syringe. Preferably, the open end of the needle is pointed; however, needles with straight ends may be used. Preferably, the open end of the needle is beveled. When the open end of the needle is beveled, it is preferred that the evaporator is attached to the longer side of the beveled opening. The needle of the syringe comprises two ends: a first, open end which is attached to the evaporator, and a second end, which is attached to the syringe tip.

The evaporator may comprise any porous material that is capable of holding the liquid dispensed from the syringe, while at the same time permitting evaporation of the liquid at a constant rate. It is preferred that the evaporator be comprised of a material having a high surface area, to facilitate evaporation of the liquid. Preferably, the evaporator comprises a piece of felt; however, materials such as cotton or synthetic cloth, glass wool or cellulose are suitable. The felt may be a natural material such as cotton, or it may be a synthetic material. Alternatively, the evaporator may comprise a rigid material such as a porous ceramic. Optionally, the evaporator may be contained within a housing.

The evaporator is affixed to the open end of the needle. In a preferred embodiment, the evaporator is attached to the needle using an epoxy adhesive; however, any appropriate means of attaching the evaporator to the end of the needle may be used.

The method of the present invention comprises the step of applying pressure to the syringe such that the plunger of the syringe moves at a constant rate, thereby delivering liquid at a constant rate from the syringe to the evaporator. In other words, the method of the invention comprises the step of delivering, i.e., transferring liquid from the syringe to the evaporator at a constant rate. Any suitable means of applying pressure to the syringe may be used. However, it is preferred that a device specifically designed to apply pressure to the syringe plunger is used. In other words, it is preferred that a device is used that has the ability to push the plunger of the syringe such that the plunger moves continuously at a constant rate or speed, thereby dispensing liquid from the syringe at a constant rate. Any device that can push the plunger of the syringe at a constant rate may be used. Preferably, a syringe actuator, such as a commercially available syringe pump, for example, a Sage Syringe Pump, such as Model 365, is used to dispense liquid from the syringe at a constant rate. In addition, syringe pumps such as those commercially available from Cole-Parmer are suitable for use with the present invention.

The apparatus and method of the present invention are suitable for generating moisture or vapor standards in a variety of matrix gases, including nitrogen, argon, helium, oxygen and hydrogen. The apparatus and method of the present invention may also be used to generate moisture or vapor standards in reactive gases such as ammonia ($NH_3$) and carbon monoxide (CO), and in corrosive gases such as hydrogen chloride (HCl) or hydrogen bromide (HBr). However, the invention is not limited to the bulk gases (i.e., matrix gases) recited herein. The bulk gas used for generating the moisture standards must be very dry; e.g., its moisture level should be at least one order of magnitude, preferably two orders of magnitude, below the target moisture level to be generated.

The maximum vapor concentration in the gas that may be obtained according to the method of the present invention is dependent upon a number of factors. Reducing the flow rate of the gas will increase the amount of liquid evaporated per unit of gas volume. Higher concentrations may be attained by elevating the temperature of the gas, or by providing a heat source to the evaporator. The vapor concentration may also be varied by varying the size of the evaporator, or by adding additional evaporators. However, the use of an evaporator having a larger area may result in a decrease in the responsiveness of the system to varying injection rates, i.e. the system may take longer to reach equilibrium after the injection rate is changed.

Additional embodiments, advantages and novel features of the present invention will be apparent to those skilled in the art from the following non-limiting examples.

6. EXAMPLES

6.1. Example of Receptacle for Inserting the Apparatus of the Present Invention into a Flowing Gas Stream Referring to FIG. 1A, a receptacle 10 for inserting the apparatus of the present invention into a flowing gas stream was constructed from soldered copper tubing having a diameter of 0.5 inch (about 1.3 cm) and various fittings. The entire receptacle from inlet 1 to outlet 2 was 17.4 inches (about 44.2 cm) long. Stainless steel screens 5 and 6 were installed at a distance of 2 and 3.3 inches (about 5 and about 8.4 cm), respectively, from the inlet 1 to serve as gas flow straighteners. The purpose of these straighteners was to reduce any eddies resulting from entrance effects of the dry gas that may impinge on the felt evaporator. Reducing eddies is thought to provide a more spatially and temporally even moisture distribution through out the flowing gas.

Figure 2:
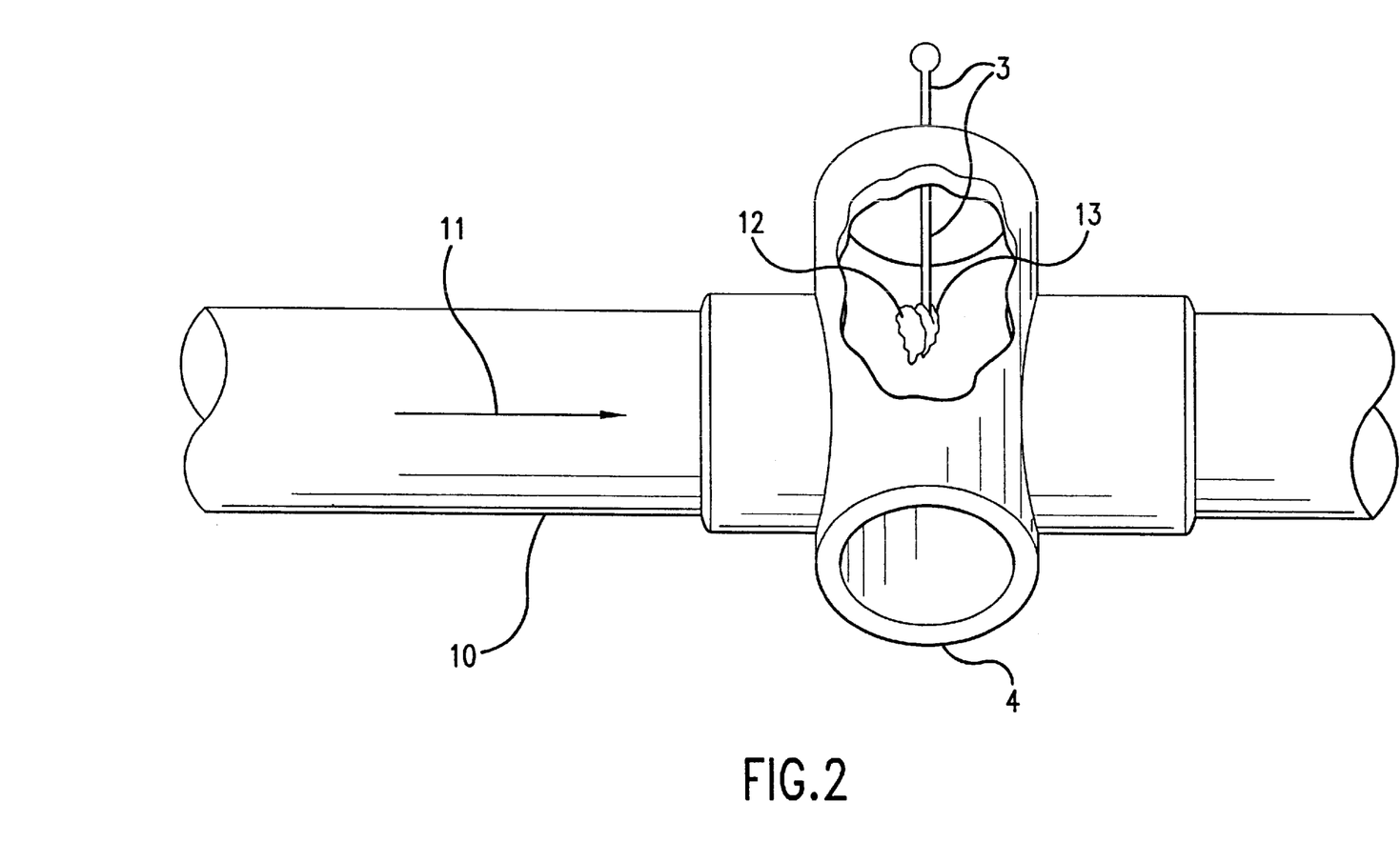
FIG. 2 is a cut-away view of the interior of the receptacle 10 of FIG. 1A, containing the flowing gas stream 11. The evaporator 12 is attached to the end of the needle 3 using epoxy adhesive 13.

FIG. 2 shows a cutaway view of the interior of the receptacle of FIG. 1A. In the interior of the device is located the evaporator 12, which comprises a circular piece of synthetic felt approximately 0.4 inches (about 1 cm) in diameter attached to one side of the open end of a syringe needle 3. The beveled opening of the needle was placed flat against the back of the felt, and an epoxy adhesive 13 was used to fix it in place. The side without epoxy was placed facing into the flow of the dry gas stream. The viewing port 4 allowed visible inspection of the felt and interior of the receptacle to verify the total evaporation of water. Were the rate of injection of water into the felt exceeded the maximum evaporation rate, visible droplets of water were readily observed.

Using the above-described apparatus, a maximum water concentration in nitrogen gas of about 600 parts per million by volume (ppmv) could be obtained under ambient conditions, using nitrogen at a nominal flow rate of 2 L/min (2.2 L/min actual rate).

Using the conditions described above, higher maximum concentrations can be attained by elevating the temperature of the dry nitrogen or providing a heat source to the evaporator in the vicinity of the felt. Other options for increasing the maximum water concentration include increasing the felt diameter, or adding additional areas of felt. The option will work as long as the water can diffuse from the point where the needle introduces it to other areas of felt. The trade-off in using too large an area of felt is that the responsiveness of the system to varying injection rates would decrease (i.e., the system would require a longer time for re-equilibration). It should be noted that the geometry and overall size of the evaporator may be varied to accommodate various flow requirements.

6.2. Another Example of Receptacle for Inserting the Apparatus of the Present Invention into a Flowing Gas Stream A receptacle for the needle and evaporator was constructed from a gas chromatography "T." A felt evaporator was placed in the straight leg of the T, and a needle was inserted into the felt from the perpendicular leg of the T. Using a dry gas at a flow rate of 100 ml/min. introduced through the straight leg of the T, water concentrations of from about 1 to about 100 ppm were easily and constantly generated.

6.3. Generation of a Calibration Curve Using the Method and Apparatus of the Present Invention In order to demonstrate the advantages of the volumetric evaporator of the present invention, an FTIR moisture analysis experiment was performed, using a Nicolet Magna 760 FTIR spectrometer outfitted with a Photonics Pathfinder 10 meter cell which was constructed of nickel plated 316L stainless steel (SS), gold mirrors on 316L stainless steel blanks, Viton o-rings and KBr windows. The spectrometer in its entirety was kept inside a closed plastic bag constantly purged with approximately 25 L/min. of purified nitrogen. The purified nitrogen was produced by passing gaseous nitrogen, obtained from a liquified source, through a Nanochem Model L-60 solid-state purifier, commercially available from Matheson Gas Products. The purified nitrogen contained less than 0.1 ppm water.

Figure 3:
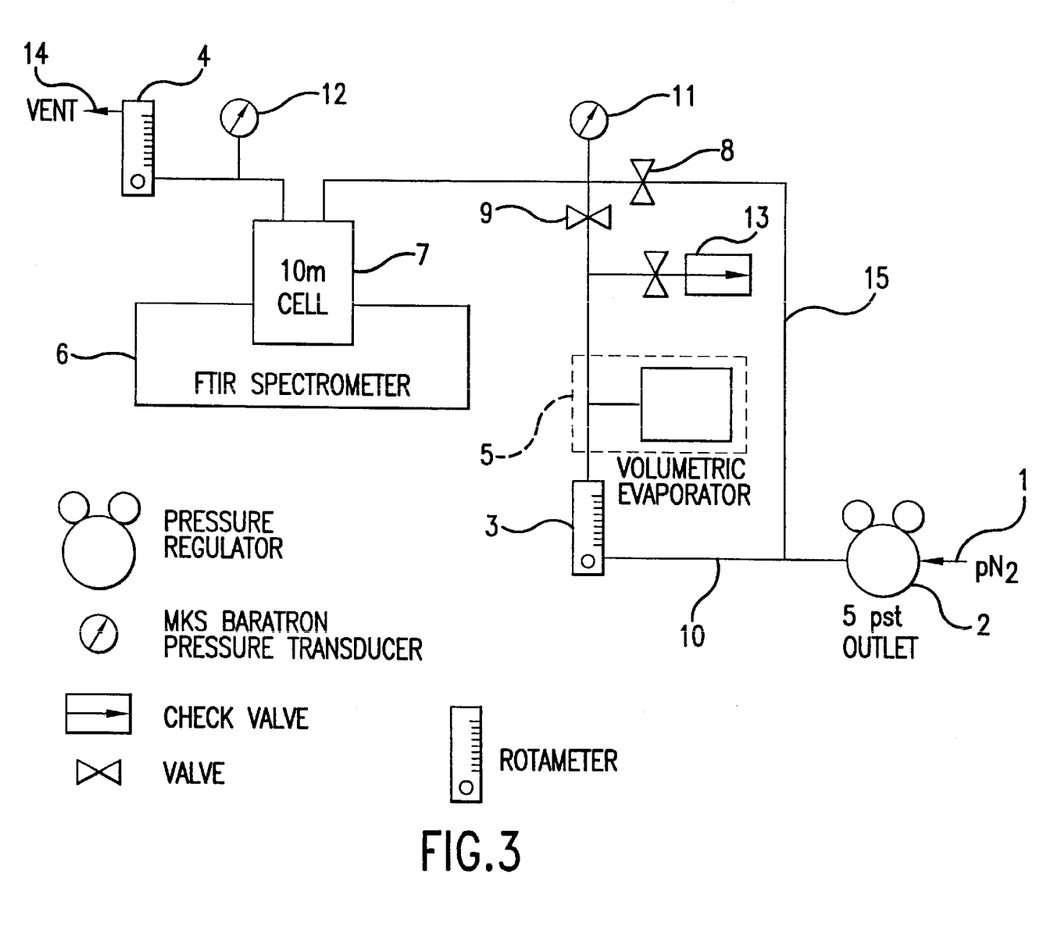

The experimental setup, shown in FIG. 3, employed valves 8 and 9 that allowed purified nitrogen to pass directly into the FTIR cell 7 (i.e., when valve 8 is open and valve 9 is closed), in order to obtain blank or zero reference measurements, or through the volumetric evaporator 5 of the present invention to be humidified (i.e., when valve 8 is closed and valve 9 is open).

The volumetric moisture generating apparatus of the present invention was configured in the following manner: The syringe actuator, a Sage Syringe Pump Model 365, drove 2.5-ml and 250-µl gas-tight Hamilton syringes, which were used to provide a wide range of water concentrations. In particular, using these two syringes, constant moisture concentrations ranging from 10 to 543 ppm were achieved. The pressure on the inlet and outlet sides of the FTIR cell was measured by separate MKS Baratron pressure transducers, 11 and 12, respectively. The flow rate was measured by a rotameter 4 (i.e., a flow meter) that led to vent 14. All stainless steel tubing was employed for gas flow.

Downstream of the Baratron gauge 11, the stainless steel tubing was maintained at 110° C. by a heating tape and insulated by aluminum foil in order to minimize the effects of moisture adsorption and desorption on the tubing walls. Such adsorption and desorption can cause a type of hysteresis in the system with a very long time constant. The FTIR spectrometer 6 was cooled by liquid nitrogen. The FTIR cell 7 was held at 637 torr pressure at 61 ° C. The nitrogen stream flowing through the moisture generator 5 of the invention was set at a 2.2 L/min flow rate (2.0 L/min nominal).

The entire flow system and cell were purged with dry nitrogen for 24 hours to obtain a zero reading before commencing the experiment. After obtaining a stable zero reading in the FTIR for the dry nitrogen, the syringe pump (actuator) was turned on to start the injection of liquid water into the evaporator. The onset of moisture in the initially dry nitrogen was determined by an increase in the 3853 cm$^{-1}$ absorbance peak for water. A stable value of absorbance indicated that the adsorption of moisture on the tubing or desorption of moisture from the tubing and other apparatus had fully equilibrated with the moisture in the nitrogen derived from the evaporator.

The calculation of moisture level in the gas stream based on the syringe reading was performed as follows. The change in syringe volume, as indicated by the syringe volume markings, at a given time interval was translated to rate by dividing the volume by the time. This rate was calculated in units of µl/hr, and then converted to µg/min. by multiplying by 16.67. The actual concentration C, in ppm, of moisture delivered was calculated as follows:

$$C = \frac{10^6 \times H_2O \text{ flow}}{N_2 \text{ flow}} = \frac{(X \text{ µg/min.}) \times (22.4 \text{ L/mol}) \times (1 \text{ mol}/18 \text{ g } H_2O) \times (10^{-6} \text{ g/µg}) \times (10^6/M)}{2.2 \text{ L } N_2/\text{min.}}$$

where X is the rate of introduction of water into the flowing dry gas stream. Various moisture levels were attained by appropriate choice of the pump setting. Table 1 lists the moisture levels in ppm in chronological order of formation, along with syringe readings (µl/hr), pump setting and FTIR scan range for each moisture level.

Figure 4:
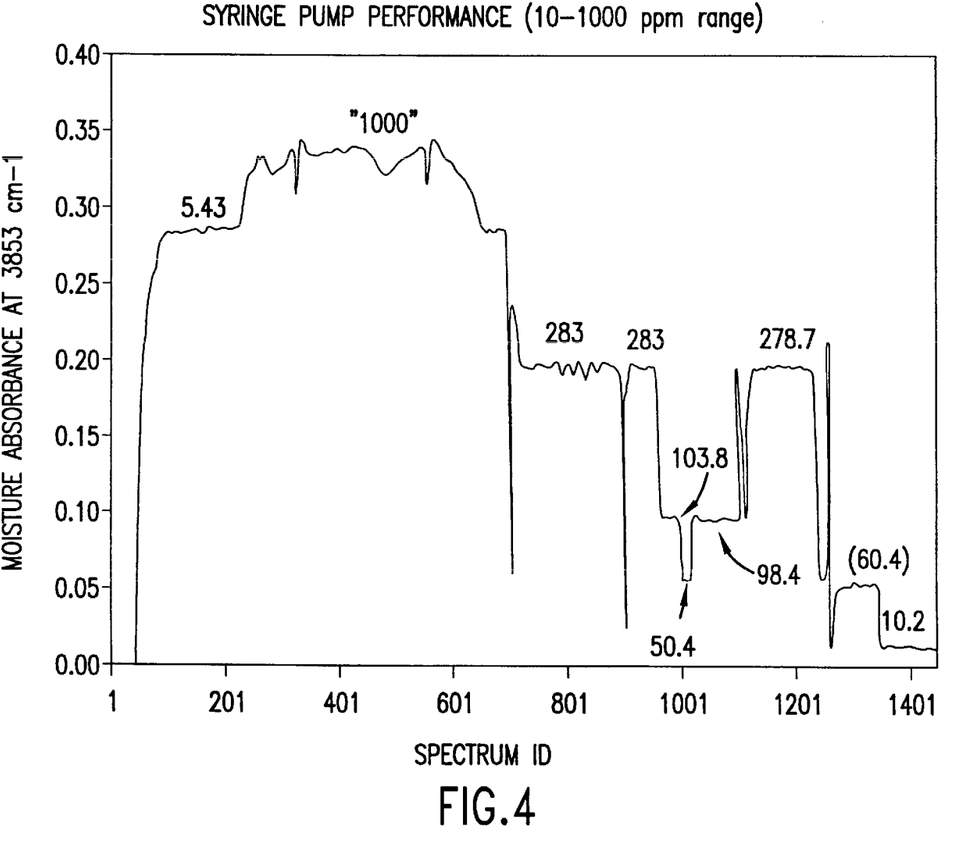
FIG. 4 is a graph depicting the progress of the FTIR measurements described in Example 6.3 as a function of scan number. The x-axis represents the scan number, and the y-axis represents the relative absorbance of the moisture peak at 3853 cm$^{-1}$.

FIG. 4 demonstrates the progress of the FTIR measurement as a function of scan number. The first concentration of water that the volumetric moisture standard generator was set for, using the 2.5-ml syringe, was 543 ppm. Then, a 1000 ppm moisture challenge was attempted, but could not be stably generated because the amount of liquid delivered to the evaporator exceeded the maximum rate of evaporation under the operating conditions employed. At a syringe pump setting corresponding to a 1000 ppm challenge, liquid droplets accumulating in the evaporator were observed through the viewing port. The absorbance at this syringe pump setting indicated a water concentration of about 650 ppm and was very unstable.

The next concentration of water generated was 283 ppm. This 283 ppm challenge was initially generated using the 2.5-ml syringe. Testing the time response of the apparatus, the effect of reloading the syringe, and the effect of changing the syringe size were all achieved through one operation. This operation involved disconnecting the 2.5-ml syringe and connecting the loaded 250-µl syringe while the flow of the carrier nitrogen gas through the moisture generator receptacle was stopped and dry nitrogen was passed through the FTIR cell via the bypass line. Changing the syringe in this manner took about 1–2 minutes to complete. A rapid decrease in the FTIR absorbance due to the diminishing moisture was observed. Upon resuming the flow of nitrogen through the volumetric moisture generator receptacle, the absorbance quickly reflected the 283 ppm challenge again. Because the cross-section of the 250-$\mu$l syringe is 10 times smaller than that of the 2.5-ml syringe, the actuator setting was changed to be 10 times faster to deliver the same 283 ppm moisture level (see Table 1).

The remainder of the absorbance data in FIG. 4 demonstrates that the volumetric moisture generating system (which includes the volumetric moisture generator of the present invention, connecting tubing, valves and pressure gauges) and the measuring system (which includes the FTIR spectrometer and cell) quickly responded to changes in the water vapor challenge and provided reproducible absorbance values. It is important to note that regardless of whether a given concentration was approached from a higher or lower preceding concentration, the system rapidly equilibrated to a reproducible, stable absorbance. This result indicates that all the water metered out by the volumetric moisture generator was evaporated and accounted for by the FTIR, thus demonstrating that the volumetric moisture generator is useful for primary standards.

Table 2 summarizes absorbance measurements at different moisture levels. Very reproducible and reliable absorbance values were obtained for concentrations in the range of 10–550 ppm, as demonstrated by the very low standard deviation (i.e., <5%). There was, however, a consistent and constant increase in percent standard deviation as a function of decreasing the moisture challenge. While absorbance values could be generated for concentrations lower than 10 ppm, the standard deviation of the data for these lower moisture challenges exceeded 5%.

Figure 5:
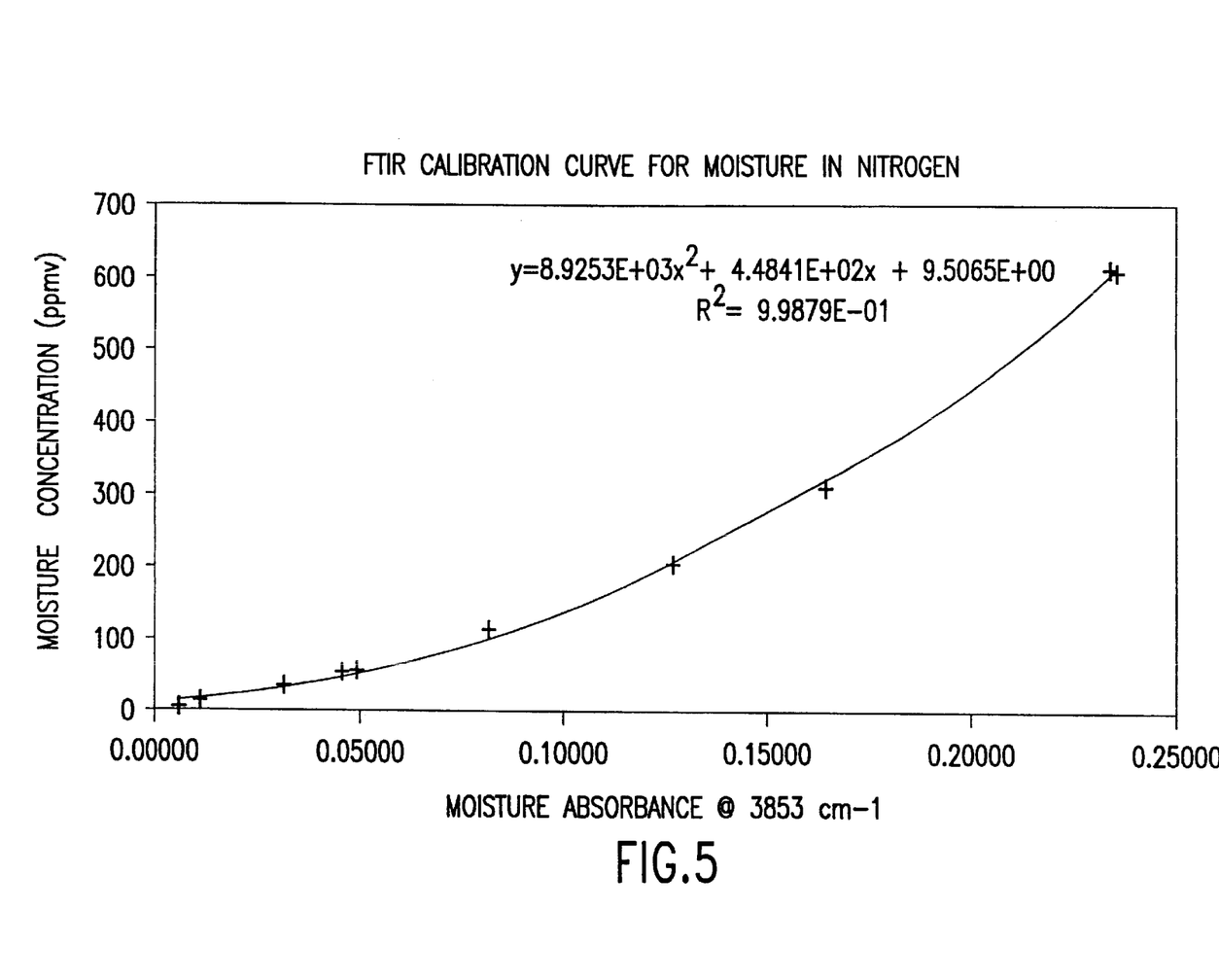
FIG. 5 is a graph depicting an FTIR moisture calibration curve obtained from the data acquired in Example 6.3. The x-axis represents the relative absorbance of the moisture peak at 3853 cm$^{-1}$. The y-axis represents the moisture concentration in ppmv as determined using the volumetric moisture generator in accordance with the methods and apparatus of the invention. The three-term polynomial regression gives $R^2$=0.999.
Figure 6:
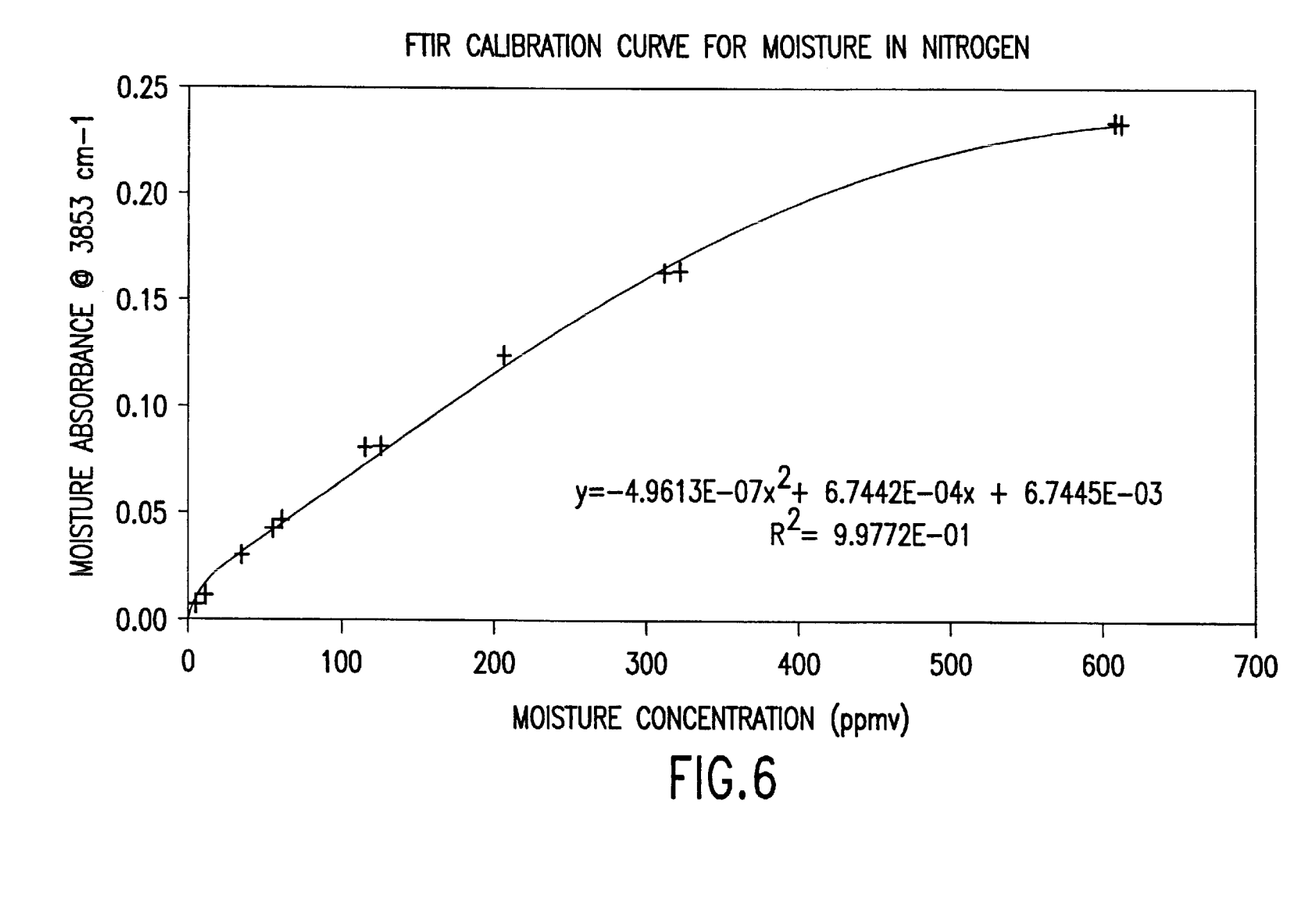
FIG. 6 is a graph depicting the FTIR moisture calibration curve obtained from the data acquired in Example 6.3 with the concentration and absorbance represented by opposite axes compared to FIG. 5. The x-axis represents the moisture concentration in ppmv as determined using the volumetric moisture generator in accordance with the methods and apparatus of the invention. The y-axis represents the relative absorbance of the moisture peak at 3853 cm$^{-1}$. The $R^2$ of the curve is 0.998.

FIGS. 5 and 6 depict the FTIR calibration curves obtained from the data acquired in this experiment. The $R^2$ value of approximately unity for each curve indicates an excellent fit of the data to the second-order polynomial curve chosen. The nonlinearity of the calibration curve appears to be in conflict with linear calibration curves which have been reported in the literature. For example, in Pivonka, Don E., "The Infrared Spectroscopic Determination of Moisture in HCl for the Characterization of HCl Gas Drying Resin Performance," *Applied Spectroscopy* 45(4):597–602 (1991), moisture streams were obtained using a GC Industries moisture generator based on diffusion of moisture vapor through a membrane, and the calibration curve obtained using a Nicolet Model 740 FTIR with a 10 m cell was linear over moisture concentrations of 0–25 ppm (see FIG. 4 of that reference). It is believed that the nonlinear calibration curve obtained using the volumetric moisture generator of the present invention more accurately reflects nonlinear absorption as a function of water concentration, caused by interactions between water molecules. However, it is possible that the non-linearity of the calibration curves obtained results from an artifact of the FTIR settings. See, P. Jaakkola et al., "Instrumental Resolution Considerations for Fourier Transform Infrared Gas-Phase Spectroscopy," *Applied Spectroscopy* 51(8):1159–1169 (1997). In any case, the method and apparatus of the present invention provide reproducible absorbance and rapid equilibration, rendering the method and apparatus of the present invention useful in the generation of primary moisture standards.

TABLE 1

Moisture Generation and Measurement in Example 3

| Syringe | Pump setting | Syringe reading ($\mu$l/hr) | Moisture concentration (ppm) | FTIR scan range | Comments |
|---|---|---|---|---|---|
| 2.5 ml | x/1000 @ 17.0% | 62.7 | 592 | | |
| 2.5 ml | x/1000 @ 17.0% | 57.5 | 543 | | |
| 2.5 ml | x/1000 @ 17.0% | 58.9 | 556 | 100–233 | |
| 2.5 ml | x/1000 @ 28.0% | | | | Droplet formed |
| 2.5 ml | x/1000 @ 25.0% | | | | Droplet stayed after 30 min. |
| 2.5 ml | x/1000 @ 5.0% | | | 339 | Droplet disappeared after 45 min. |
| 2.5 ml | x/1000 @ 25.0% | | | | Droplet formed again |
| 2.5 ml | x/1000 @ 5.0% | | | | Droplet eliminated after 40 min. |
| 2.5 ml | x/1000 @ 17.0% | 58.6 | 553 | 570–703 | |
| 2.5 ml | x/1000 @ 8.5% | 30.1 | 284 | 717–898 | |
| 250 $\mu$l | x/100 @ 8.5% | 30.0 | 283.2 | 898–956 | |
| 250 $\mu$l | x/1000 @ 30.0% | 11 | 103. | 956–995 | |
| 250 $\mu$l | x/1000 @ 15.0% | 5.35 | 50.4 | 995–1010 | |
| 250 $\mu$l | x/1000 @ 30.0% | 10.4 | 98.4 | 1010–1110 | |
| 250 $\mu$l | x/100 @ 8.5% | 29.5 | 278.7 | 1110–1230 | |
| 250 $\mu$l | x/1000 @ 15.0% | (6.4) | (60.4) | 1230–1342 | 10–20% error in rate since measured for only 1 hour |
| 250 $\mu$l | x/1000 @ 3.0% | 1.08 | 10.2 | 1342–1998 | pump OFF |
| 250 $\mu$l | x/1000 @ 0.1% | 0.033 | 0.314 | 2246–2666 | Restart at pump minimum |
| 250 $\mu$l | x/1000 @ 1.5% | 0.423 | 4.0 | 2666–2775 | |
| 250 $\mu$l | x/1000 @ 3.0% | 1.09 | 10.3 | 2775–2923 | |
| 250 $\mu$l | x/1000 @ 1.5% | 0.55 | 5.2 | 2923–3103 | |
| 250 $\mu$l | x/1000 @ 9.0% | 3.22 | 30.4 | 3103–3267 | |
| 250 $\mu$l | x/1000 @ 55.0% | 18.3 (avg.) | 173.0 | 3267–3350 | |
| 250 $\mu$l | x/1000 @ 9.0% | 3.01 | 28.4 | 3350– | |

TABLE 2

FTIR Average Corrected Absorbance (3583 cm$^{-1}$)

| Moisture challenge (ppm) | Spectrum scan number range | Corrected absorbance average | Standard deviation | Percent standard deviation |
|---|---|---|---|---|
| 10.2 | 1347–1686 | 0.01339 | 0.00065 | 4.83 |
| (60.4) | 1275–1342 | 0.05603 | 0.00133 | 2.37 |
| 55.4* | | | | |
| 98.4 | 1017–1099 | 0.10120 | 0.00087 | 0.86 |

TABLE 2-continued

FTIR Average Corrected Absorbance (3583 cm$^{-1}$)

| Moisture challenge (ppm) | Spectrum scan number range | Corrected absorbance average | Standard deviation | Percent standard deviation |
|---|---|---|---|---|
| 278.7 | 1135–1222 | 0.20472 | 0.00126 | 0.62 |
| 556 | 10–234 | 0.28969 | 0.00155 | 0.54 |

*value taken from earlier scans since 60.4 is based 1 hour interval and is not accurate.

Figure 7:
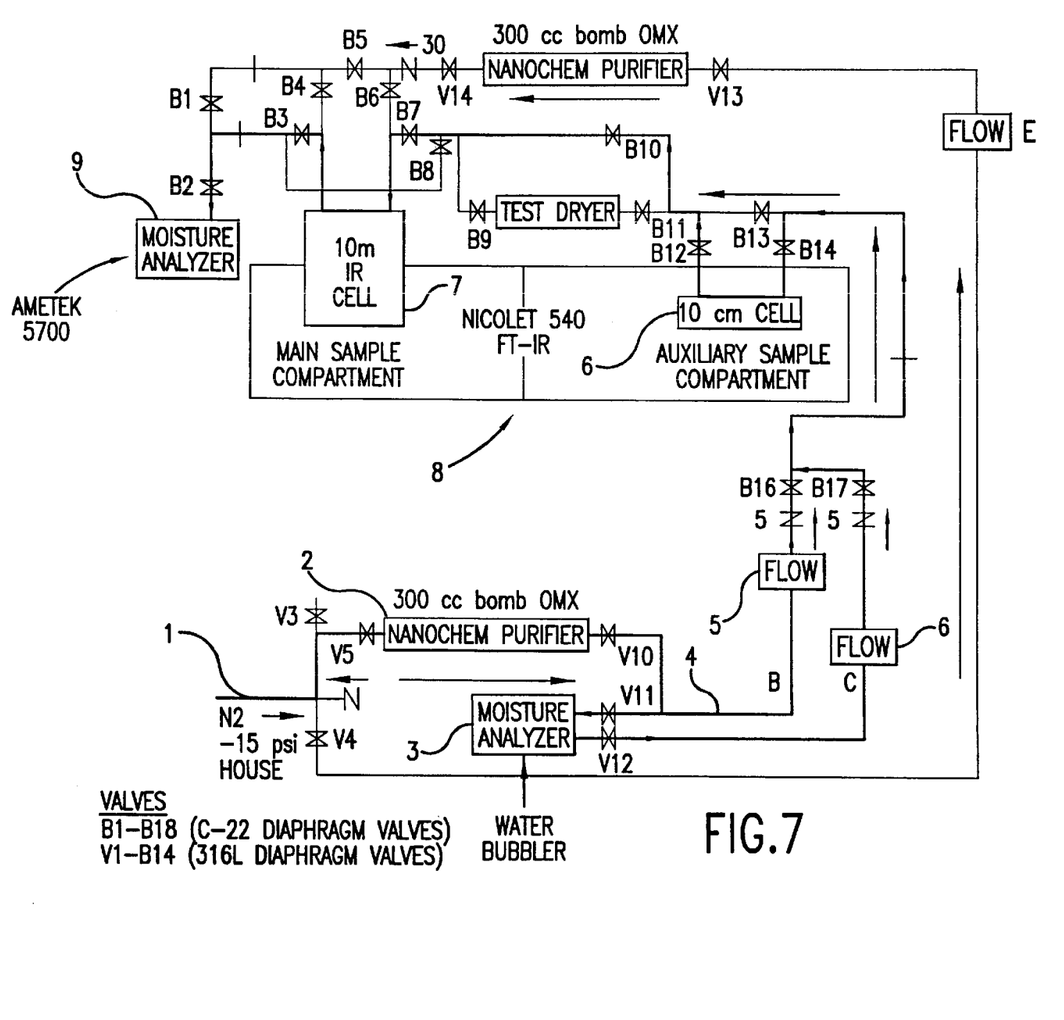
FIG. 7 is a schematic view of the experimental system used in Example 6.4, in which the generation of linear and non-linear moisture calibration curves using 10 cm and 10 m FTIR gas cells in an FTIR instrument were investigated. The system employed nitrogen source 1, which was dried by passing it through a gas drier 2 (300 cc bomb OMX Nanochem purifier). The system was constructed so that a portion of the dry nitrogen flowed through a moisture generator 3, which in this case was a water bubbler, and the other portion of the dry nitrogen flowed through gas line 4 comprising flowmeter 5. The water-saturated nitrogen gas stream exiting from the moisture generator 3, flowed through flowmeter 6, and was then diluted with the dry nitrogen stream from gas line 4 to provide a nitrogen stream having the desired moisture level. The nitrogen stream having the desired moisture level was delivered first to a 10 cm cell 6 and then to a 10 m cell 7 located in a Nicolet 540 FTIR instrument 8, and eventually to an Ametek 5700 moisture analyzer 9.

6.4. Investigation of Linear and Non-linear Moisture Calibration Curves Obtained in an FTIR Instrument: Comparison of 10 Centimeter Cell and 10 Meter Cell To further investigate the question of non-linear water absorption in the FTIR, the following comparative moisture analysis experiment was conducted. A system as described in FIG. 7 was used for this experiment. The system employed nitrogen source 1, which was dried by passing it through a gas drier 2 (300 cc bomb OMX Nanochem purifier). The system was constructed so that a portion of the dry nitrogen flowed through a moisture generator 3, which in this case was a water bubbler, and the other portion of the dry nitrogen flowed through gas line 4 comprising flowmeter 5. The water-saturated nitrogen gas stream exiting from the moisture generator 3, flowed through flowmeter 6, and was then diluted with the dry nitrogen stream from gas line 4 to provide a nitrogen stream having the desired moisture level. The nitrogen stream having the desired moisture level was delivered first to a 10 cm cell 6 and then to a 10 m cell 7 located in a Nicolet 540 FTIR instrument 8, and eventually to an Ametek 5700 moisture analyzer 9.

Figure 8:
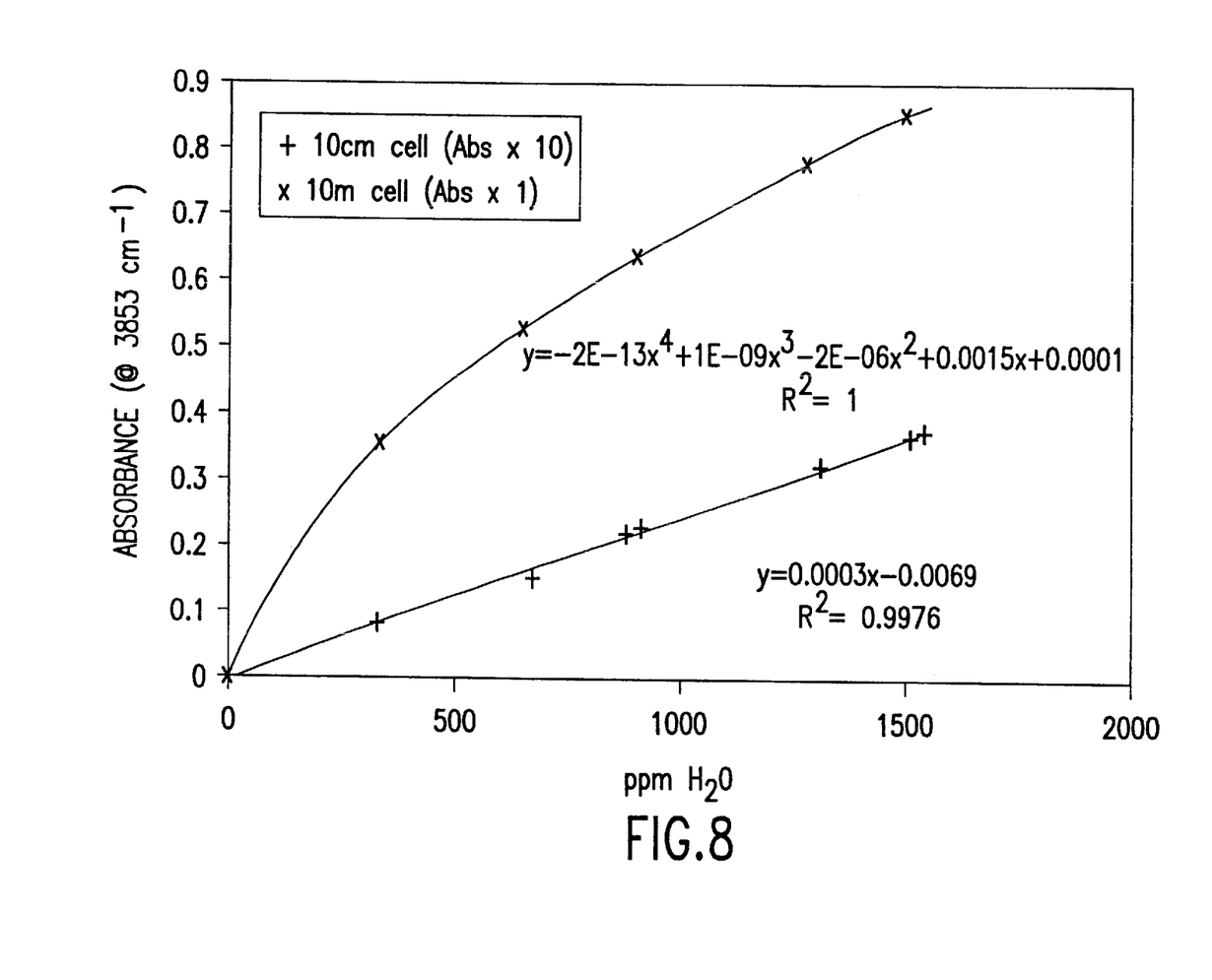
FIG. 8 is a graph which depicts the FTIR calibration curves obtained in Example 6.4 with the 10 cm and 10 m cells under identical operating conditions. The data points of the calibration obtained using the 10 m cell are represented by squares, and the data points of the calibration curve obtained using the 10 cm cell are represented by diamonds. The x-axis represents ppm $H_2O$, as determined by an Ametek 5700 moisture analyzer, and the y-axis represents the FTIR absorbance of the moisture peak at 3853 cm$^{-1}$.

The moisture level readings of the Ametek 5700 and the corresponding absorbance of the 3853 cm$^{-1}$ water peak on the FTIR obtained using the the 10 cm cell are listed in Table 3. Average values are listed in Table 4. Data for the 10 meter cell and respective average values are listed in Tables 5 and 6. FIG. 8 shows the calibration curves obtained with the 10 cm and 10 m cells under identical operating conditions using the average values in Tables 4 and 6, respectively. The linear calibration curve of the 10 cm cell is in agreement with the linear calibration curve obtained by Pivonka, Don E., "The Infrared Spectroscopic Determination of Moisture in HCl for the Characterization of HCl Gas Drying Resin Performance," *Applied Spectroscopy* Vol. 45, No. 4, pp. 597–602 (1991) (see FIG. 8 of that reference) using the less accurate moisture generator based on diffusion through a membrane. In contrast, the nonlinear calibration curve of the 10 m cell is in accord with that obtained in Example 6.3 above.

TABLE 3

Data Obtained Using 100–900 ppm H$_2$O Calibration Range on Ametek 5700 Moisture Analyzer and 10 cm FTIR Cell For Capacity Analysis

| FTIR Scan ID no. | ppm H$_2$O (as determined by Ametek 5700 Moisture Analyzer) | FTIR Absorbance Of Moisture Peak at 3853 cm$^{-1}$ |
|---|---|---|
| 980207 | 0.724 | 0.00000 |
| CM0001 | 338.4 | 0.00786 |
| CM0002 | 336.5 | 0.00781 |
| CM0003 | 336.9 | 0.00777 |
| CM0004 | 684.2 | 0.01710 |
| CM0005 | 675.1 | 0.01690 |
| CM0006 | 680.2 | 0.01660 |
| CM0007 | 678.8 | 0.01630 |
| CM0008 | 680.6 | 0.01161 |
| CM0009 | 678.0 | 0.01620 |
| CM0010 | 920.6 | 0.02280 |
| CM0011 | 918.1 | 0.02260 |
| CM0012 | 916.5 | 0.02200 |
| CM0013 | 893.1 | 0.02210 |
| CM0014 | 890.2 | 0.02180 |
| CM0015 | 887.3 | 0.02150 |
| CM0016 | 1312 | 0.03250 |
| CM0017 | 1310 | 0.03240 |
| CM0018 | 1311 | 0.03240 |
| CM0019 | 1525 | 0.03690 |
| CM0020 | 1519 | 0.03740 |
| CM0021 | 1512 | 0.03800 |
| CM0022 | 1542 | 0.03830 |
| CM0023 | 1545 | 0.03810 |
| CM0024 | 1547 | 0.03820 |

TABLE 4

Data Obtained Using 100–900 ppm H$_2$O Calibration Range on Ametek 5700 Moisture Analyzer and 10 cm FTIR Cell For Capacity Analysis: Average Results for Graph of Calibration

| ppm H$_2$O (as determined by Ametek 5700 Moisture Analyzer) | FTIR Absorbance Of Moisture Peak at 3853 cm$^{-1}$ |
|---|---|
| 0.0 | 0.0047 |
| 337.3 | 0.0078 |
| 679.1 | 0.0147 |
| 918.4 | 0.0225 |
| 890.2 | 0.0218 |
| 1311 | 0.0324 |
| 1518 | 0.0374 |
| 1544 | 0.0382 |

TABLE 5

Data Obtained Using 100–900 ppm H$_2$O Calibration Range on Ametek 5700 Moisture Analyzer and 10 cm FTIR Cell For Capacity Analysis

| FTIR Scan ID no. | ppm H$_2$O (as determined by Ametek 5700 Moisture Analyzer) | FTIR Absorbance Of Moisture Peak at 3853 cm$^{-1}$ |
|---|---|---|
| CA0001 | 336.9 | 0.360 |
| CA0002 | 335.8 | 0.360 |
| CA0003 | 334.1 | 0.358 |
| CA0004 | 568.2 | 0.541 |
| CA0005 | 686.5 | 0.539 |
| CA0006 | 683.7 | 0.538 |
| CA0007 | 849.1 | 0.654 |
| CA0008 | 929.7 | 0.652 |
| CA0009 | 924.5 | 0.651 |
| CA0010 | 1181 | 0.789 |
| CA0011 | 1312 | 0.791 |
| CA0012 | 1314 | 0.790 |
| CA0013 | 1445 | 0.857 |
| CA0014 | 1515 | 0.859 |
| CA0015 | 1523 | 0.863 |

TABLE 6

Data Obtained Using 100–900 ppm H$_2$O Calibration Range on Ametek 5700 Moisture Analyzer and 10 m FTIR Cell For Capacity Analysis: Average Results for Graph of Calibration

| ppm H$_2$O (as determined by Ametek 5700 Moisture Analyzer) | FTIR Absorbance Of Moisture Peak at 3853 cm$^{-1}$ |
|---|---|
| 0 | 0.038 |
| 335.6 | 0.3593 |
| 646.1 | 0.5393 |
| 901.1 | 0.6523 |
| 1269 | 0.7900 |
| 1494 | 0.8597 |

The present invention is not to be limited in scope by the specific embodiments and examples described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

We claim:

1. An apparatus for introducing a preselected amount of a vaporized liquid into a flowing gas stream at a constant rate, which comprises:

(a) a syringe having a needle attached thereto;
   (b) an evaporator, said evaporator being attached to one end of said needle, wherein the evaporator may be located in the flowing gas stream; and
   (c) a means for compressing the syringe at a constant speed, such that the liquid to be vaporized is delivered at a constant rate from the syringe through the needle into the evaporator and into said flowing gas stream to produce a gas stream that is less than saturated.

2. The apparatus of claim 1 wherein the evaporator comprises a piece of felt.

3. The apparatus of claim 1 wherein the needle comprises a beveled opening and the evaporator is attached to the longer side of the beveled opening.

4. The apparatus of claim 1 wherein the evaporator is attached to the needle using an epoxy adhesive.

5. The apparatus of claim 1 wherein the means for compressing said syringe at a constant speed comprises a syringe actuator.

6. The apparatus of claim 1 further comprising a means for heating the evaporator.

7. The apparatus of claim 1 wherein the liquid to be vaporized is an organic liquid.

8. The apparatus of claim 7 wherein the organic liquid is selected from the group consisting of acetone, methylene chloride, acetonitrile, benzene, and toluene.

9. The apparatus of claim 1 wherein the liquid to be vaporized is an organometallic liquid.

10. An apparatus for introducing a preselected amount of water vapor into a flowing gas stream at a constant rate, which comprises:

(a) a syringe having a needle attached thereto;
    (b) an evaporator, said evaporator being attached to one end of said needle, wherein the evaporator may be located in the flowing gas stream; and
    (c) a means for compressing the syringe at a constant speed, such that water is delivered at a constant rate from the syringe through the needle into the evaporator and into said flowing gas stream to produce a gas stream that is less than saturated.

11. The apparatus of claim 10 wherein the evaporator comprises a piece of felt.

12. The apparatus of claim 10 wherein the evaporator is attached to the needle using an epoxy adhesive.

13. The apparatus of claim 10 wherein the needle comprises a beveled opening and the evaporator is attached to the longer side of the beveled opening.

14. The apparatus of claim 10 wherein the means for compressing said syringe at a constant speed comprises a syringe actuator.

15. The apparatus of claim 10 further comprising a means for heating the evaporator.

16. A method for introducing a preselected amount of a vaporized liquid into a flowing as stream at a constant rate, which comprises:

(a) providing a syringe having a needle attached thereto, wherein the syringe contains the liquid to be vaporized; and
    (b) compressing the syringe at a constant speed, such that an amount of the liquid to be vaporized is transferred at a constant rate from the syringe through the needle into an evaporator, said evaporator being attached to one end of the needle and situated in the flowing gas stream, whereby the liquid simultaneously evaporates from the evaporator into the flowing gas stream at said constant rate, wherein the amount of vaporized liquid is selected to result in a preselected concentration of the vaporized liquid in the flowing gas stream.

17. The method of claim 16 wherein the evaporator comprises a piece of felt.

18. The method of claim 16 wherein the evaporator is attached to the needle using an epoxy adhesive.

19. The method of claim 16 wherein the needle comprises a beveled opening and the evaporator is attached to the longer side of the beveled opening.

20. The method of claim 16 further comprising the step of heating the evaporator.

21. The method of claim 16 wherein the liquid to be vaporized is an organic liquid.

22. The method of claim 21 wherein the organic liquid is selected from the group consisting of acetone, methylene chloride, acetonitrile, benzene, and toluene.

23. The method of claim 16 wherein the liquid to be vaporized is an organometallic liquid.

24. A method for introducing a preselected amount of water vapor into a flowing gas stream at a constant rate, which comprises:

(a) providing a syringe having a needle attached thereto, wherein the syringe contains liquid water; and
    (b) compressing the syringe at a constant speed, such that an amount of water to be vaporized is transferred at a constant rate from the syringe through the needle into an evaporator, said evaporator being attached to one end of the needle and situated in the flowing gas stream, whereby the water simultaneously evaporates from the evaporator into the flowing gas stream at said constant rate, wherein the amount of water is selected to result in a preselected concentration of water vapor in the flowing gas stream.

25. The method of claim 24 wherein the evaporator comprises a piece of felt.

26. The method of claim 24 wherein the evaporator is attached to the needle using an epoxy adhesive.

27. The method of claim 24 wherein the needle comprises a beveled opening and the evaporator is attached to the longer side of the beveled opening.

28. The method of claim 24 further comprising the step of heating the evaporator.

29. The method of claim 24 wherein the preselected concentration of water vapor in the flowing gas stream is about 1 ppb to about 10,000 ppm.

30. The method of claim 24 wherein the preselected concentration of water vapor in the flowing gas stream is about 10 ppb to about 1000 ppm.

31. The method of claim 24 wherein the preselected concentration of water vapor in the flowing gas stream is about 10 ppb to about 800 ppm.

32. An apparatus for generating a moisture standard, comprising:
 (a) a syringe having a needle attached thereto;
 (b) an evaporator, said evaporator being attached to one end of said needle, wherein the evaporator is located in a flowing gas stream; and
 (c) a means for compressing the syringe at a constant speed, such that the liquid to be vaporized delivered at a constant rate from the syringe through the needle into the evaporator, wherein the amount of liquid delivered to the evaporator is below a level that would saturate said flowing gas stream with said vaporized liquid to produce a gas stream that is less than saturated.

33. A method for generating a moisture standard, comprising:
 (a) providing a flowing gas stream;
 (b) providing a syringe having a needle attached thereto, wherein the syringe contains the liquid to be vaporized;
 (c) compressing the syringe at a constant speed, such that an amount of the liquid to be vaporized is transferred at a constant rate from the syringe through the needle into an evaporator, said evaporator being attached to one end of the needle and situated in the flowing gas stream, wherein all of the transferred liquid evaporates from the evaporator into the flowing gas stream and the amount of vaporized liquid is below the saturation level of the flowing gas stream to produce a gas stream that is less than saturated.

\* \* \* \* \*